United States Patent
Rasmussen

(10) Patent No.: US 7,270,124 B2
(45) Date of Patent: Sep. 18, 2007

(54) INHALER

(75) Inventor: Jörgen Rasmussen, Struer (DK)

(73) Assignee: AstraZeneca AB, Södertalje (SE)

( * ) Notice: Subject to any disclaimer, the term of this patent is extended or adjusted under 35 U.S.C. 154(b) by 621 days.

(21) Appl. No.: 10/221,711

(22) PCT Filed: Mar. 16, 2001

(86) PCT No.: PCT/SE01/00558

§ 371 (c)(1),
(2), (4) Date: Dec. 19, 2002

(87) PCT Pub. No.: WO01/70314

PCT Pub. Date: Sep. 27, 2001

(65) Prior Publication Data

US 2003/0116155 A1    Jun. 26, 2003

(30) Foreign Application Priority Data

Mar. 18, 2000  (GB) .................................. 0006526.8

(51) Int. Cl.
*A61M 15/00* (2006.01)
(52) U.S. Cl. .............................. 128/200.23; 128/200.14
(58) Field of Classification Search ........... 128/200.15, 128/200.23, 200.12, 203.15, 203.19, 200.14; 239/338; 222/162, 402.1, 402.11, 402.13, 222/402.2

See application file for complete search history.

(56) References Cited

U.S. PATENT DOCUMENTS

| | | | |
|---|---|---|---|
| 3,456,644 A | 7/1969 | Thiel | |
| 3,456,645 A | 7/1969 | Brock | |
| 3,636,949 A | 1/1972 | Kropp | ........................ 128/173 |
| 5,031,610 A * | 7/1991 | Armstrong et al. | .... 128/200.23 |
| 5,060,643 A | 10/1991 | Rich et al. | ............. 128/200.23 |

(Continued)

FOREIGN PATENT DOCUMENTS

| | | |
|---|---|---|
| EP | 0 186 280 | 7/1986 |
| GB | 1 269 811 | 4/1972 |
| GB | 22928901 | 3/1996 |
| WO | WO99/49916 | 10/1999 |
| WO | WO 00/16835 | 3/2000 |
| WO | WO 00/16838 | 3/2000 |

OTHER PUBLICATIONS

MSN Encarta Dictionary Definition of "cam"; Printed Dec. 10, 2004.*

*Primary Examiner*—Justine Yu
(74) *Attorney, Agent, or Firm*—Fish & Richardson P.C.

(57) ABSTRACT

An inhaler for delivery by inhalation of a medicament from the canister which is compressible to deliver a dose of medicament. The inhaler comprises a housing (1) for holding a canister (2) having a generally cylindrical body (3) with the cylindrical axis of the body (3) in predetermined direction and a loading mechanism for loading a resilient loading element (7) which is arranged, when loaded, to bias compression of the canister (2). The loading mechanism comprises a loading member (8) engaging the resilient loading element (7) and two contact members (9) movable relative to the housing (1) in a movement direction orthogonal to said predetermined direction and arranged to drive the loading member (8) to load the resilient loading element (7), through a cam arrangement between the contact member (8). The cam arrangement may allow for the ratio of the amount of driven movement of the loading member (8) to the amount of mount of the contact members (9) to be non-linear, preferably reducing over the driven movement to compensate for the increasing resistance by the resilient loading element.

38 Claims, 12 Drawing Sheets

U.S. PATENT DOCUMENTS

| | | | |
|---|---|---|---|
| 5,217,004 A * | 6/1993 | Blasnik et al. | 128/200.23 |
| 5,447,150 A | 9/1995 | Bacon | 128/200.14 |
| 5,954,047 A | 9/1999 | Armer et al. | 128/200.23 |
| 5,971,226 A | 10/1999 | Goncalves | 222/321.6 |
| 6,405,727 B1 * | 6/2002 | MacMichael et al. | 128/203.12 |
| 6,595,205 B2 * | 7/2003 | Andersson et al. | 128/200.23 |
| 2003/0230305 A1 * | 12/2003 | Christrup et al. | 128/200.23 |

* cited by examiner

INHALER

TECHNICAL FIELD

The present application relates to an inhaler for delivery of medicament from a canister, particularly to an actuation mechanism for actuating a canister held in the inhaler.

BACKGROUND

Inhalers are commonly used to deliver a wide range of medicaments. The inhaler holds a canister of medicament which is actuatable, for example by compression, to deliver a dose of medicament. Some known inhalers are provided with an actuation mechanism for actuating the canister. The mechanism may be breath-actuated i.e. arranged to actuate the canister in response to inhalation at the mouth piece. Typically a breath-actuated inhaler includes a loading mechanism for loading a resilient loading element with an actuation force for compression of the canister. A triggering mechanism may be provided to hold the resilient loading element against compression of the canister, the triggering mechanism releasing the resilient loading element upon inhalation.

Important considerations for an actuation mechanism are reliability and simplicity. Reliability is important to ensure that the medicament is correctly delivered on every use, especially when the medicament is required by the user in an emergency. A simple structure is required firstly to assist in ensuring that the actuation mechanism operates reliably and secondly to simplify manufacture, thereby reducing manufacturing costs.

A problem often encountered, especially by elderly, young and infirm users, is that it is difficult to generate enough force to load the resilient loading element provided to bias actuation of the canister. The energy with which the resilient loading element is loaded must be sufficient to actuate the canister which can create difficulties for some users. The first aspect of the present invention is intended to assist in loading of the mechanism.

SUMMARY

According to the first aspect of the present invention, there is provided an inhaler for delivery by inhalation of a medicament from a canister which is compressible to deliver a dose of medicament, the inhaler comprising a housing for holding a canister having a generally cylindrical body with the cylindrical axis of the body in predetermined direction;
- a loading mechanism for loading a resilient loading element which is arranged, when loaded, to bias compression of the canister, the loading mechanism comprising:
  - a loading member engaging the resilient loading element; and
  - at least one contact member movable relative to the housing in a movement direction orthogonal to said predetermined direction and arranged to drive the loading member to load the resilient loading element through a cam arrangement between the at least one contact member and the loading member.

By arranging the contact member(s) to be movable relative to the housing in a movement direction orthogonal to the cylindrical axis of the body of the canister held in the housing, loading is made easier. The inhaler may be held in the palm of one hand with the body of the canister aligned generally upwardly. Sideways movement of the contact member(s) may then be easily achieved by gripping the inhaler between a finger and thumb. A cam arrangement is particularly advantageous for driving the loading member to load the resilient loading element through a cam arrangement between the contact member(s) and the loading member. It meets the requirements for both reliability and simplicity. Furthermore it allows the loading member to be suitably arranged in the inhaler when the contact member(s) have the convenient arrangement of being movable orthogonal to the predetermined direction of the axis of the canister.

In particular, the cam arrangement allows the movement of the contact member(s) to be converted into movement of the loading member in a direction orthogonal to said movement direction, i.e. in a plane parallel to the predetermined direction in which the cylindrical axis of the body of the canister is held. As a result, the resilient loading element may be simply configured to bias compression of the canister.

Desirably the loading member is driven to rotate in said direction orthogonal to said movement direction. This is advantageous because it converts the linear force provided to the contact member(s) into a rotational movement. This assists in loading of the resilient loading element and provides a simpler and more reliable mechanism than if the loading element was movable linearly, say along a track.

The resilient loading element may be a torsion spring. It may bias a canister engagement member engageable with a canister held in the housing to compress the canister which may be a lever rotatable about an axis parallel to the movement direction of the at least one contact member. Thus, a simple configuration with a reliable action is provided.

Preferably, the inhaler has two contact members disposed on opposite sides of the housing. This improves the ease of operation. The two contact members may be depressed together between a finger and a thumb with the inhaler held in the palm of a hand. An alternative would be to provide a single contact member which the user may push relative to the housing.

According to a second aspect of the present invention an inhaler for delivery by inhalation of a medicament from a canister which is compressible to deliver a dose of medicament, the inhaler comprising:
- a housing for holding a canister;
- a loading mechanism for loading a resilient loading element which is arranged, when loaded, to bias compression of the canister, the loading mechanism comprising:
  - a loading member engaging the resilient loading element; and
  - at least one contact member movable relative to the housing to drive the loading member to load the resilient loading element, the ratio of the amount of driven movement of the loading member to the amount of movement of the at least one contact member being a non-linear function of the position of the loading member.

As a result of the gearing ratio of the amount of driven movement of the loading member to the amount of movement of the contact member(s) being a non-linear function of the position of the loading member, it is possible to control the amount of force which the user needs to apply over the movement stroke of the contact member(s) relative to the housing. This technique can be used to produce a number of technical advantages.

Preferably, said ratio reduces during at least a major portion of the driven movement of the loading member. This allows compensation for the reactive force generated by the resilient biasing element which must be overcome by the user. Generally, this reactive force increases as the resilient loading element is loaded. However compensation is provided by ensuring that the gearing ratio reduces during the driven movement of the loading member which in itself reduces the amount of force required by the user.

Desirably, the ratio varies such that the necessary force applied to the at least one contact member is substantially constant. If the loading force of the resilient biasing element increases linearly (by an amount which is for example proportional to the spring constant if the resilient loading element is a spring), then a linear resistance may be achieved if the ratio is inversely proportional to the position of the loading member during said major portion of its driven movement.

Secondly, varying the ratio non-linearly with the position of the loading member can provide the inhaler with a particular feel to the user operating the contact members. For example, it is desirable that wherein said ratio is reduced during an initial portion of the driven movement of the loading member relative to the subsequent portion. In this way, the user initially feels a relatively low resistance to movement of the contact members. This not only increases the quality of the inhaler as perceived by the user, but also assists in application of force.

The second aspect of the present invention may be implemented by means of the contact member(s) driving the loading member through a non-linear cam arrangement for example with an inhaler according to the first aspect of the present invention. In fact, the first and second aspects of the present invention may be embodied by the same actuation mechanism and features associated with each aspect may be freely combined to advantage.

The first and second aspects of the present invention are particularly suitable for use in an inhaler arranged to hold the resilient loading element against actuation of the canister and triggerable to release the resilient loading element or a breath-actuated inhaler in which the triggering mechanism is arranged to be triggered by inhalation.

DESCRIPTION OF THE DRAWINGS

To allow better understanding, an inhaler which embodies the present invention will now be described by way of non-limitative example with reference to the accompanying drawings, in which.

DETAILED DESCRIPTION

Figure 1:
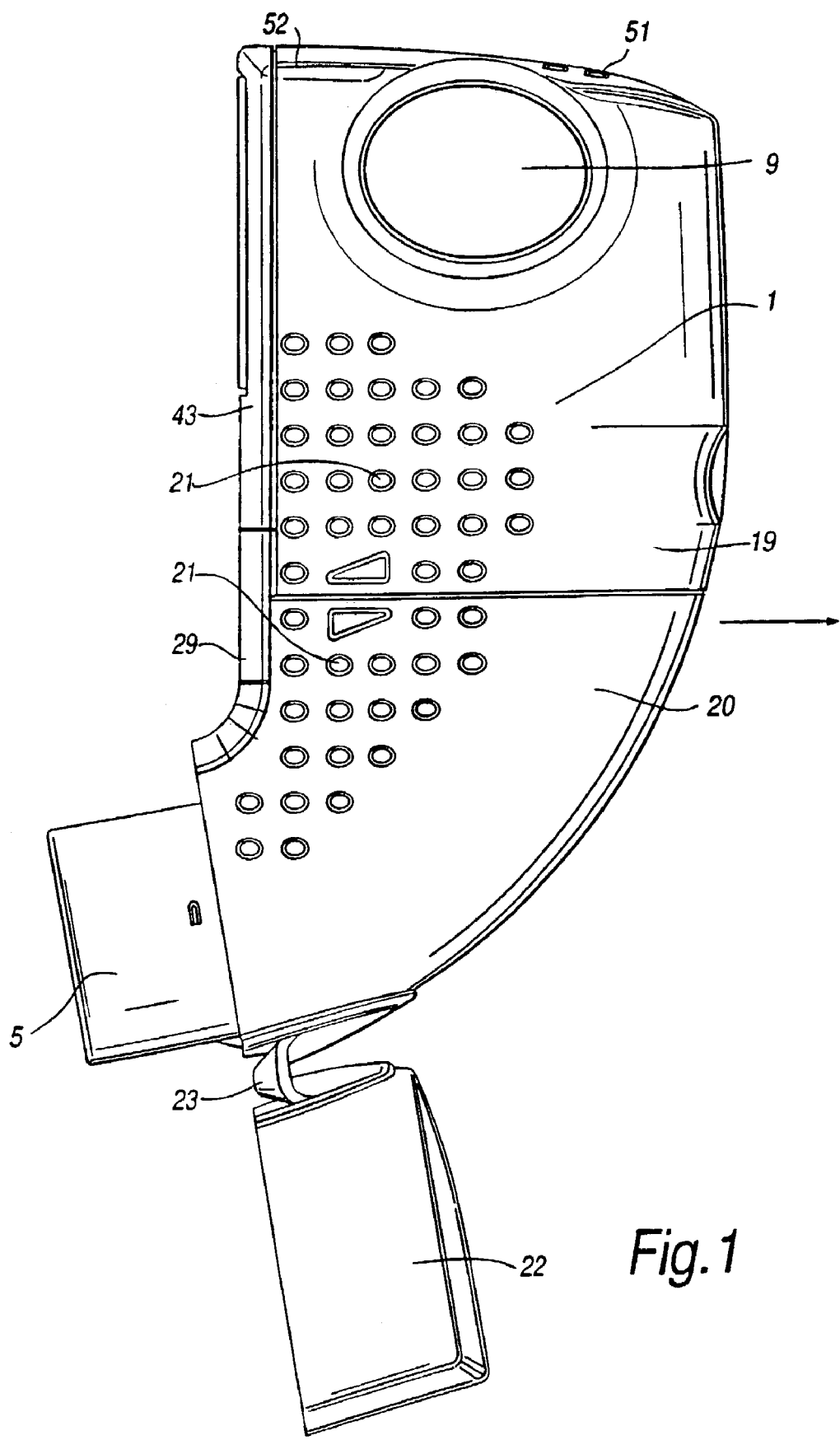
FIG. 1 is a side view of the inhaler.

As illustrated in FIG. 1, the inhaler has a housing 1 comprising an upper portion 19 and a lower portion 20. As illustrated in the cross-sectional view of FIG. 2, the upper housing portion 19 is a hollow shell which holds a canister 2 of medicament having a generally cylindrical body 3 held with its axis in a predetermined direction, vertical in FIG. 2. The upper housing portion 19 houses an actuation mechanism for actuating the canister 2 which will be described in more detail below.

The interior of the upper housing portion 19 is open to the atmosphere by means of air inlets 51 formed in the upper wall 52 of the upper housing portion 19. The location of the air inlets 51 minimises occlusion by the users hand which will normally grip the sides of the housing 1 and not cover the upper wall 52.

The canister 2 is compressible to deliver a dose of medicament. In particular the canister 2 has a valve stem 4 which is compressible relative to the body 3 to deliver a dose of medicament from the valve stem 4. The canister is of a known type including a metering chamber which captures a defined volume the medicament from the body 3 of the canister 2. This volume of medicament is delivered as a metered dose from the valve stem 4 on compression of the valve stem 4 relative to the body 3. The valve stem 4 is weakly biased outwardly by an internal valve spring (not shown) to reset the canister 2 after compression for refilling the metering chamber.

The lower housing portion 20 is a hollow shell connected to the upper housing portion 19 by a sliding joint (not shown) which allows the lower portion 20 to be separated in the direction of the arrow in FIG. 1 by the user gripping textured surfaces 21 formed on the upper and lower housing portions 19 and 20. A cap 22 is hinged to the lower housing portion 20 by a flexible joint 23 to cover and uncover a mouthpiece 5 protruding from the lower housing portion 20.

Figure 2:
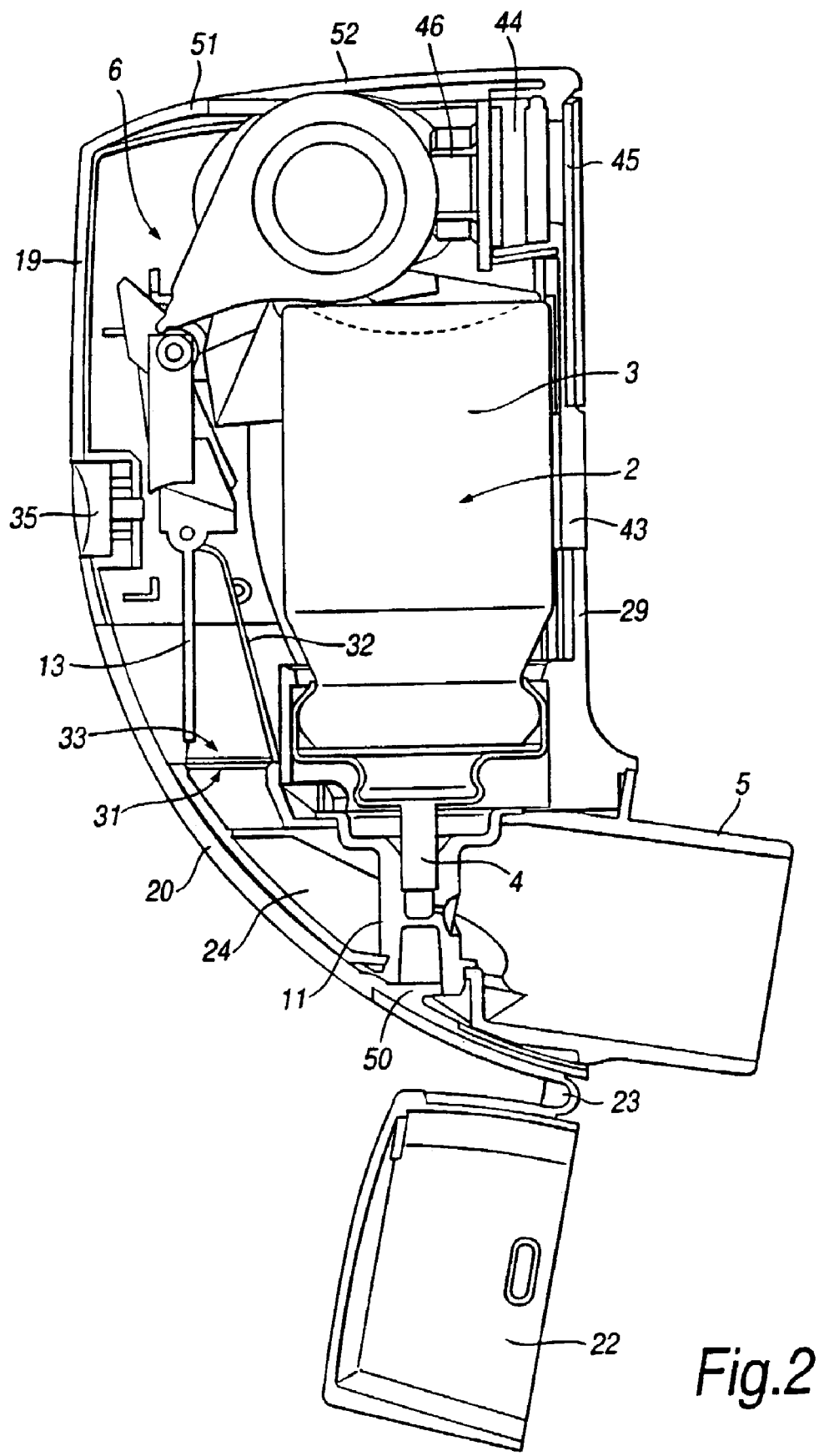
FIG. 2 is a cross-sectional view of the inhaler illustrating the housing and duct.
Figure 3:
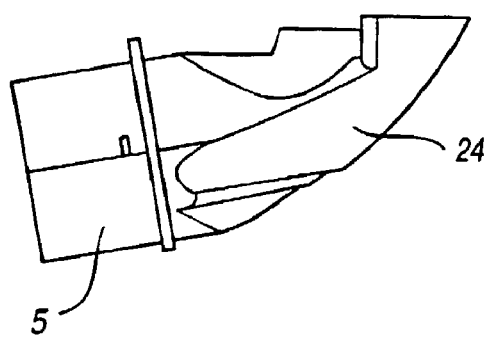
FIG. 3 is a side view of the duct.

As shown in FIG. 2, the lower housing portion 20 houses a duct 24 which is integrally formed with the mouthpiece 5, as illustrated in isolation in FIG. 3.

Figure 4:
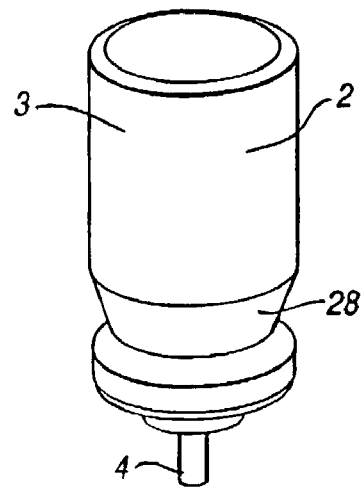
FIG. 4 is a side view of the canister and duct assembled together.
Figure 4:
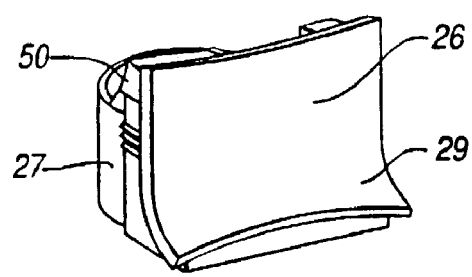
Figure 4:
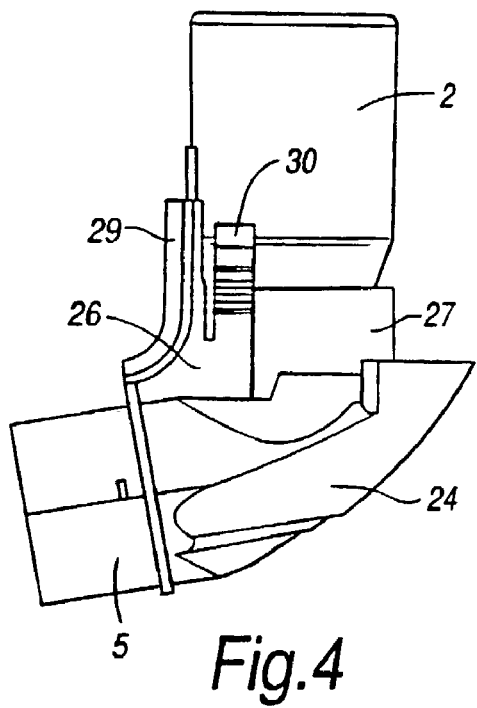
Figure 5:
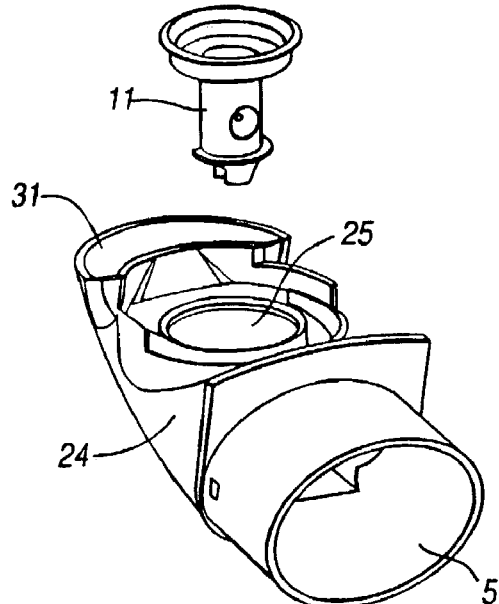
FIG. 5 is an exploded view of the canister, collar and duct.
Figure 6:
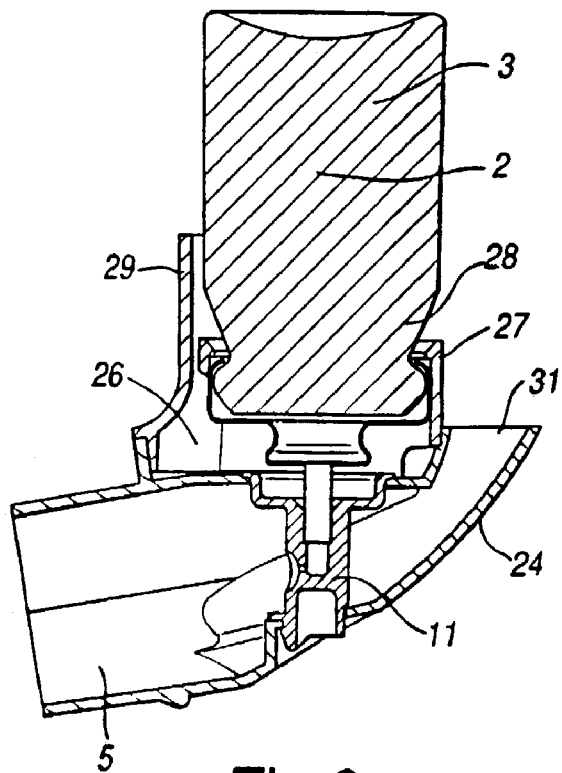
FIG. 6 is a cross-sectional view of the canister and dust assembled together.

The duct 24 is assembled with a canister 2 as shown in FIGS. 4 to 6. The duct 24 receives a nozzle block 11 in an opening 25. The valve stem 4 of the canister is received in the nozzle block 11 which is arranged to direct a dose of medicament delivered from the valve stem 4 out of the inhaler through the mouthpiece 5. The duct 24 and nozzle block 11 are separately formed. This allows each to be manufactured and subsequently assembled. This produces manufacturing and logistical savings because it facilitates different nozzle block designs being incorporated with a single duct design and vice versa.

A collar 26 is permanently connected to the canister 2. The collar 26 includes an annular retaining ring 27 permanently fitted around a necked portion 28 of the canister body 3. The retaining portion 27 prevents removal of the collar 26 from the canister such that the collar 26 is removed and replaced together with the canister 2. However, the retaining portion 27 and the canister 2 have a small degree of relative movement along the axis of the canister 5 to allow compression of the canister body 2 towards the valve stem 4.

The collar 26 further includes a front panel 29 integrally formed with the retaining ring 27. When the canister 2 is inserted in the housing 1, the front panel 29 of the collar 26 closes an opening formed between the upper housing portion 19 and the lower portion 20 and therefore forms a part of the outer wall of the housing 1. Accordingly, the presence or absence of the front panel 29 provides a visual indication to the user of whether or not a canister 2 has been inserted in the canister, because the collar 26 is permanently connected to the canister 2.

A pair of catch arms 30 integrally formed with the front panel 29 of the sides of the collar 26 catch the interior surface of the upper housing portion 19 to hold the collar 26 and the canister 2 in the upper housing portion 19.

The lower housing portion 20 has a stud 50 which locates the end of the nozzle block 11 as shown in FIG. 2 to hold the lower housing portion 20 and the duct 24 in place relative to one another. However, the lower housing portion 20 is not retained on the duct 24, so may be removed from the upper housing portion 19 leaving the canister 2 inserted in the upper housing portion 19 and the duct 24 held on the canister 2 by the valve stem 4 being inserted in the nozzle block 11. The duct 24 and nozzle block 11 may subsequently be slid off the valve stem 4 for cleaning or replacement. The canister 2 and collar 26 may be slid out from the upper housing portion 19 after depression of the catch arms 30. Subsequently a replacement canister 2 and collar 26 may be inserted.

Typically a new duct 24 and nozzle block 11 will be provided to the user with each new canister 2 so that the duct 24 and mouthpiece 5 are regularly replaced to prevent damage or dirt building up over time. The duct 24 has an opening 31 at its end opposite from the mouthpiece 5.

As shown in FIG. 2, the upper housing portion 19 holds a flap duct 32 which extends from a flow inlet 33 to a flap 13 which forms part of the triggering mechanism for the actuation mechanism as described in detail below. Therefore the duct 24 housed in the lower housing portion 19 and the flap duct 32 together define a composite duct shaped to direct the inhalation flow from the mouthpiece 5 to the flap 13. The composite duct formed by the duct 24 and the flap duct 32 is shaped to control the flow to the flap 13 to provide appropriate flow characteristics for proper operation of the flap 13.

The inhaler is further provided with an actuation mechanism 6. To assist understanding, a general description of the overall structure and operation of the actuation mechanism 6 will first be given.

An actuation force for compressing the canister 2 is stored in a resilient loading element in the form of a torsion spring 7. To load the torsion spring 7, the actuation mechanism 6 includes a loading mechanism consisting of a loading member in the form of a rotatable spindle 8 and two contact members in the form of buttons 9 which protrude from the housing as shown in FIG. 1. Depression of the buttons 9 towards one another, relative to the housing 1, drives the loading member 8 to load the torsion spring 7 through a cam arrangement between the buttons 9 and spindle 8.

The torsion spring 7 biases compression of the canister 2 by engaging a canister engagement member in the form of a lever 10 which depresses the body 3 of the canister towards the stem 4 held in the nozzle block 11.

To allow storage of the actuation force in the torsion spring 7 after loading, the actuation mechanism 6 includes a triggering mechanism. This includes a locking lever 12 which holds the canister engagement lever 10 against compression of the canister 2. To release the canister engagement lever 10, the triggering mechanism further includes a vane in the form of a flap 13 which in a rest state holds the locking lever 12 in place. Inhalation at the mouthpiece 5 moves the flap 13 to release the locking member 12. This in turn releases the canister engagement lever 10 allowing the torsion spring 7 to drive compression of the canister 2.

The actuation mechanism 6 further includes a locking mechanism which locks the spindle 8 after loading of the torsion spring 7, thereby holding the torsion spring 7 in its loaded state before triggering and locking the canister in its compressed state after triggering.

The locking mechanism includes a catch 14 which, in a locking position, catches the spindle 8 and holds the torsion spring 7 in its loaded state. The locking mechanism further includes an intermediate member 15. A resilient biasing element in the form of a spring 16 is provided between the catch 14 and the intermediate member 15 to bias the catch 14 towards its locking position. The spring 16 allows deflection of the catch 14 by the spindle 8 during loading of the torsion spring 7.

Prior to inhalation the intermediate member 15 is held in place by the canister engagement lever 10. Upon inhalation at the mouthpiece 5, the flap 13 engages the intermediate member 15 to hold it in place. After compression by the canister engagement lever 10, the canister 2 is locked in its compressed state by the catch 14 of the locking mechanism holding the spindle 8 in place.

When the level of inhalation at the mouthpiece falls below a predetermined threshold, the flap 13 releases the intermediate member 15 to unload the biasing element 16 which in turn allows the catch 14 to release the spindle 8. After release by the catch 14, the spindle 8, torsion spring 7 and canister engagement lever 10 move upwardly and the canister resets.

Figure 7:
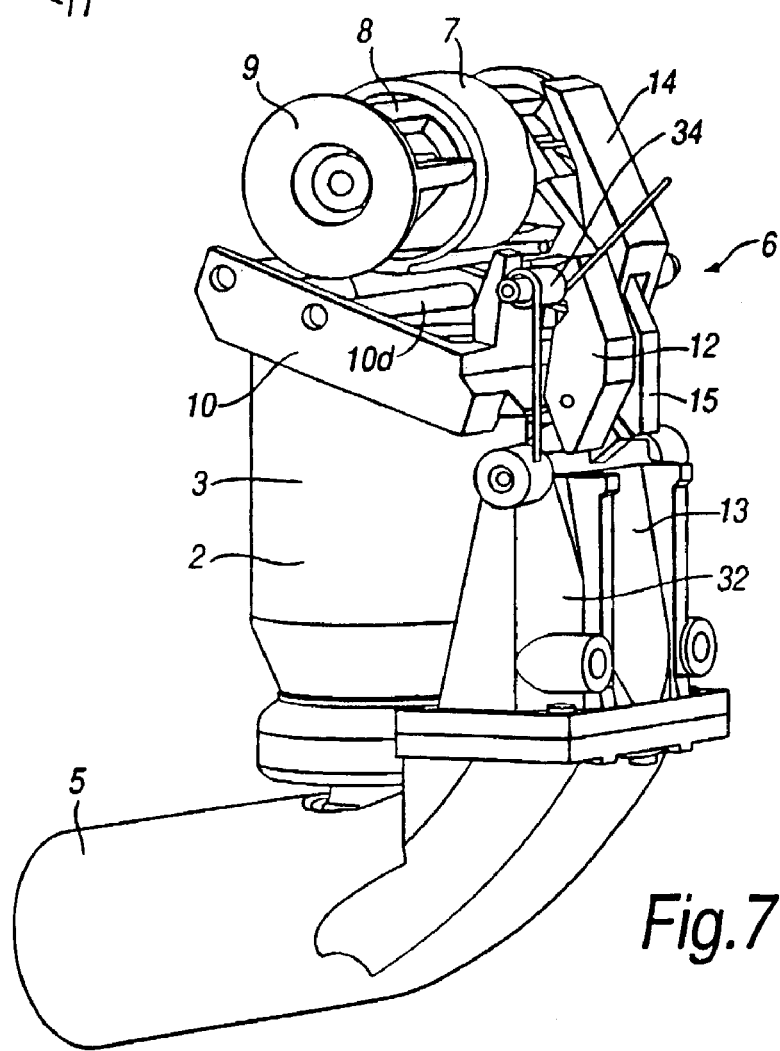
FIG. 7 is a view from the side and rear of the actuation mechanism.

Now there will be given a detailed description of the actuation mechanism 6, the entirety of which is illustrated in FIG. 7 and parts of which are illustrated in FIGS. 8 to 13.

Figure 8:
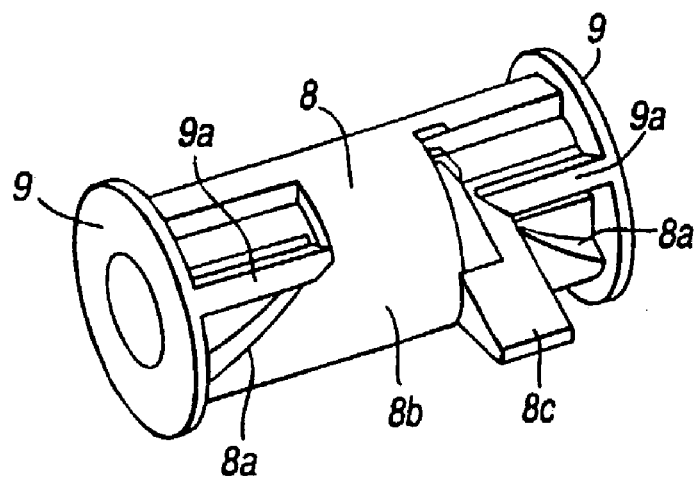
FIG. 8 is a view from the rear of the spindle.

The loading mechanism is illustrated in FIG. 8 and consists of a rotatable spindle 8 and two contact members in the forms of buttons 9 at both ends. The spindle 8 is rotatably mounted in the upper housing portion 19 about an axis orthogonal to the axis of the cylindrical body 3 of the canister 2. The spindle 8 has a pair of cam surfaces 8a disposed on opposite sides of the rotational axis of the spindle 8. The buttons 9 are mounted in the housing to be movable in a movement direction parallel to the rotational axis of the spindle 8. The buttons 9 each have a pair of inwardly projecting cam followers 9a which each engage a respective cam surface 8a of the spindle 8. The cam arrangement of the cam surfaces 8a and the cam followers 9a between the spindle 8 and the buttons 9 causes depression of the buttons 9 to drive rotation of the spindle 8.

Figure 9:
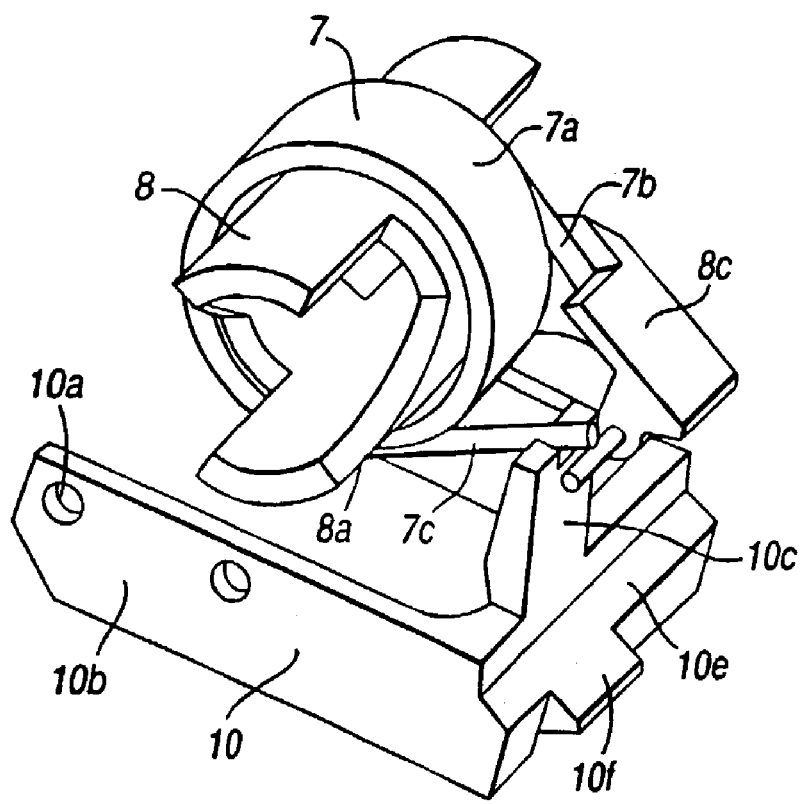
FIG. 9 is a view from the side, rear and above showing the arrangement of the resilient loading element.

As illustrated in FIG. 9, the torsion spring 7 which forms the resilient loading element is disposed with its coils 7a encircling a central cylindrical surface 8b of the spindle 8. A catch arm 8c protrudes radially from the spindle 8. A first leg 7b of the torsion spring 7 is restrained by the catch arm 8c so that the movement of the spindle 8 driven by the buttons 9 loads the torsion spring 7.

Figure 10:
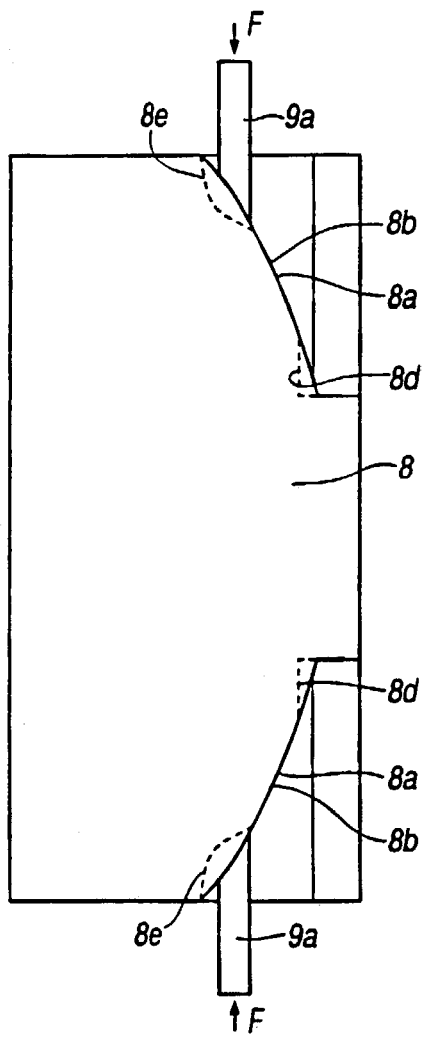
FIG. 10 is a schematic view of the cam surfaces formed on the spindle.

As illustrated schematically in FIG. 10, the cam surfaces 8a have a non-linear shape which causes the gearing ratio of the amount of driven movement of the spindle 8 to the amount of movement of the buttons 9 to be a non-linear function of the rotational position of the spindle 8. The major portion 8b of each cam surface 8a is shaped with increasing pitch to compensate for the increased reactive loading force applied by the torsion spring 7 to the spindle 8 as the buttons 9 are depressed. In particular, they are shaped such that the necessary force applied to the buttons is substantially constant so the user feels a linear resistance. As the torsion spring 7 has a linear spring constant, this is achieved by shaping the major portion 8*b* of each cam surface 8*a* such that the gearing ratio is inversely proportion to the rotational position of the spindle 8.

Optionally, the outermost portion of the cam surfaces 8*a* which are contacted by the cam followers 9*a* during the initial portion of the driven movement of the spindle may have a decreased pitch, for example as illustrated by the dotted lines 8*e*. This is to reduce the gearing ratio relative to the subsequent major portion 8*b*. In this way the user initially feels a low resistance to movement of the buttons 9. This improves the feel perceived by the user and also assists the user in applying force.

Another option is to provide the final portion of the cam surface 8*a* with a detent, for example as illustrated by the dotted lines 8*d*. When the end of the cam followers 9*a* reach the detent 8*d*, the cam surface 8*a* of the spindle 8 no longer exerts a force urging the buttons outwardly on the buttons 9. At this position the detent 8*d* is urged by the torsion spring 7 against the side of the cam followers 9*a* and therefore holds the buttons 9 in their innermost position. This prevents the buttons 9 from loosely sliding back and forth after the torsion spring 7 has been loaded.

As shown in FIG. 9, the torsion spring 7 engages a canister engagement lever 10 which is pivotally mounted to the interior of the housing about an axis 10*a*. The canister engagement lever 10 is generally U-shaped with two parallel sides 10*b* by a cross piece 10*c*. A bar 10*d* extending between the two sides 10*b* bears on the body 5 of the canister 2. A mount 10*e* formed on the cross-piece 10*c* is engaged by the second leg 7*c* of the torsion spring 7, whereby loading of the torsion spring 7 biases the lever 10 to compress the canister 2. The canister engagement lever 10 is biased upwardly by a reset spring (not shown), which may be arranged as a torsion spring on the axis 10*a*, but this is weaker than the torsion spring 7.

The torsion spring 7, spindle 8 and canister engagement lever 10 are all rotatable about axis orthogonal to the cylindrical axis of the body 5 of the canister 2. This provides a simple and reliable loading mechanism particularly because of the arrangement of the torsion spring 7 with its coils 7*a* encircling the spindle 8. Some or all of these elements could alternatively be linearly movable in a plane parallel to the cylindrical axis of the body 5 of the canister 2 to achieve a loading mechanism which is equally simple to construct. However rotatable elements are preferred from the point of view of reliability in repeated use of the actuation mechanism 6.

On the other hand, the movement of the buttons in a direction orthogonal to the cylinder axis of the body 3 of the canister 2 assists the user in application of force to the loading mechanism. As typical for inhalers, the housing 1 extends in the direction of the cylindrical axis of the body 3 of the canister 2, so may be easily held in the palm of a hand with the buttons 9 protruding from either side. Thus the buttons 9 are easily depressed between a finger and thumb. Alternatively a single button could be provided allowing loading in a similar manner by the user pressing the button and the housing on the opposite side to the button. Either configuration also allows loading by laying the inhaler on a surface and applying force for example with the palm of a hand. This facilitates loading by a user with limited finger control or movement, for example a chronic arthritis sufferer.

Figure 11:
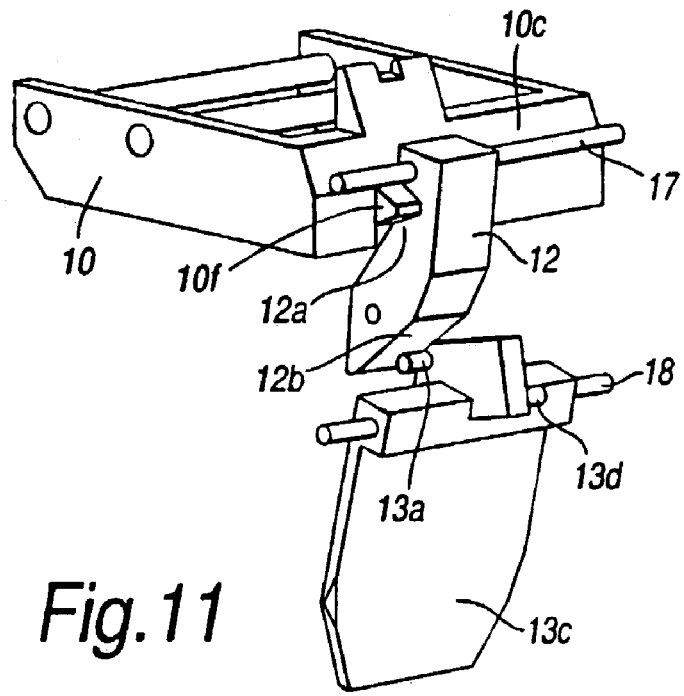
FIG. 11 is a view from the side and rear of the triggering mechanism.
Figure 12:
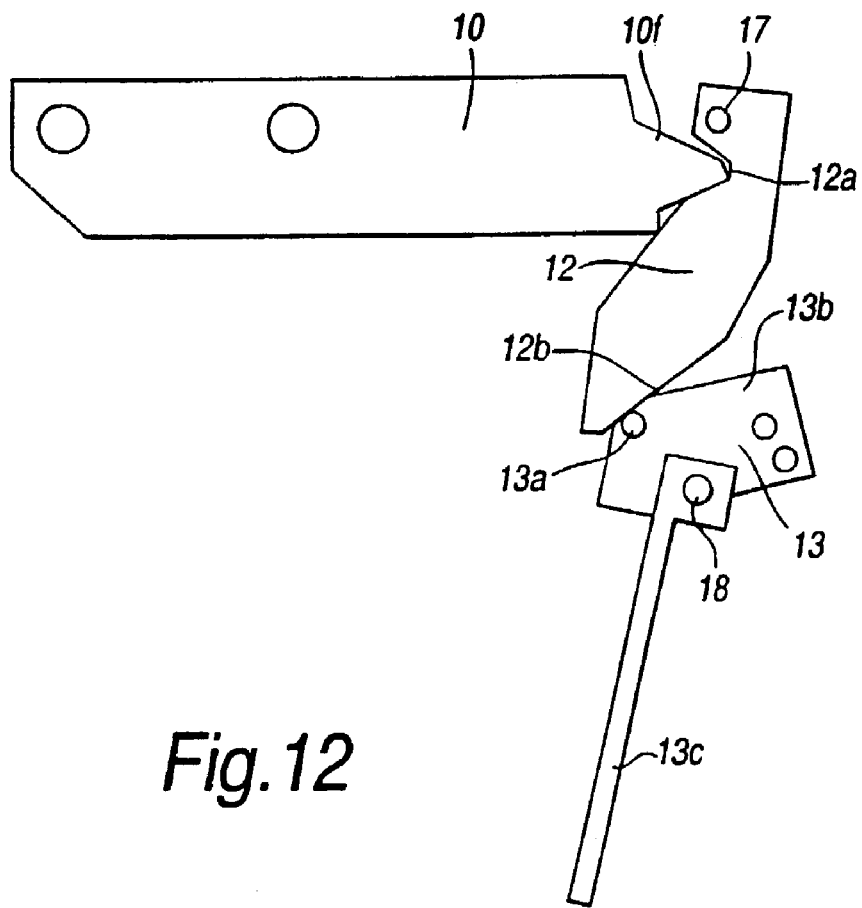
FIG. 12 is a side view of the triggering mechanism.

The actuation member mechanism 6 includes a triggering mechanism as illustrated in FIGS. 11 and 12 which allows storage of the actuation force in the torsion spring 7 after loading.

The triggering mechanism includes a locking lever 12 which is pivotably mounted on an axle 17 extending across the interior of the housing 1. The locking lever 12 has a notch 12*a* adjacent the axle 17. In a reset state shown in FIG. 12, the notch 12*a* holds a protrusion 10*f* protruding from the cross-piece 10*c* of the canister engagement lever 10, thereby holding the lever 10 against compression of the canister 2. The locking lever 12 is weakly biased towards the position shown in FIGS. 11 and 12 by a reset spring 34 arranged as a torsion spring on the axle 17.

The triggering mechanism further includes a vane in the form of a flap 13 which is rotatably mounted on an axle 18 extending across the interior of the housing 1. The flap 13 biased by a reset spring (not shown), which may be arranged as a torsion spring on the axle 18, towards the position shown in FIG. 12. The flap 13 has a locking lever engagement surface 13*a* which protrudes from a block 13*b* positioned above the axle 18. In the position shown in FIG. 12, the engagement surface 13*a* engages a contact surface 12*b* formed on the end of the locking lever 12 distal from the axle 17 to hold the locking lever 12 in place holding the canister engagement lever 10.

The flap 13 is disposed in the composite duct formed by the duct 24 and the flap duct 32 extending from the mouthpiece 5 with a flap portion 13*c* extending across the composite duct at the opposite end from the mouthpiece 5, where the duct opens into the interior of the housing 1. Therefore, the flap 13 is responsive to inhalation at the mouthpiece 5.

Inhalation of the mouthpiece draws the flap portion 13*c* into the flap duct 32 (clockwise in FIG. 2 and anticlockwise in FIG. 12). Such rotation of the flap 13 allows the locking lever engagement surface 13*a* to move out of contact with the contact surface 12*b* of the locking lever 12.

The upper housing portion 19 also mounts a button 35 disposed adjacent the flap 13 above the axle 18 so that depression of the button 35 rotates the flap 13 in the same direction as inhalation at the mouthpiece 5. Therefore, the button 35 allows the actuation mechanism 6 to be manually released without inhalation at the mouthpiece 5, for example to allow actuation of the canister 2 for testing.

When the canister engagement lever 10 is loaded by the torsion spring 7, release of the locking lever 12 by the flap 13 allows the canister engagement lever 10 to be driven to compress the canister 2. The protrusion 10*f* deflects the locking lever 12 (anticlockwise in FIG. 12) as the canister engagement lever 10 passes.

Figure 13:
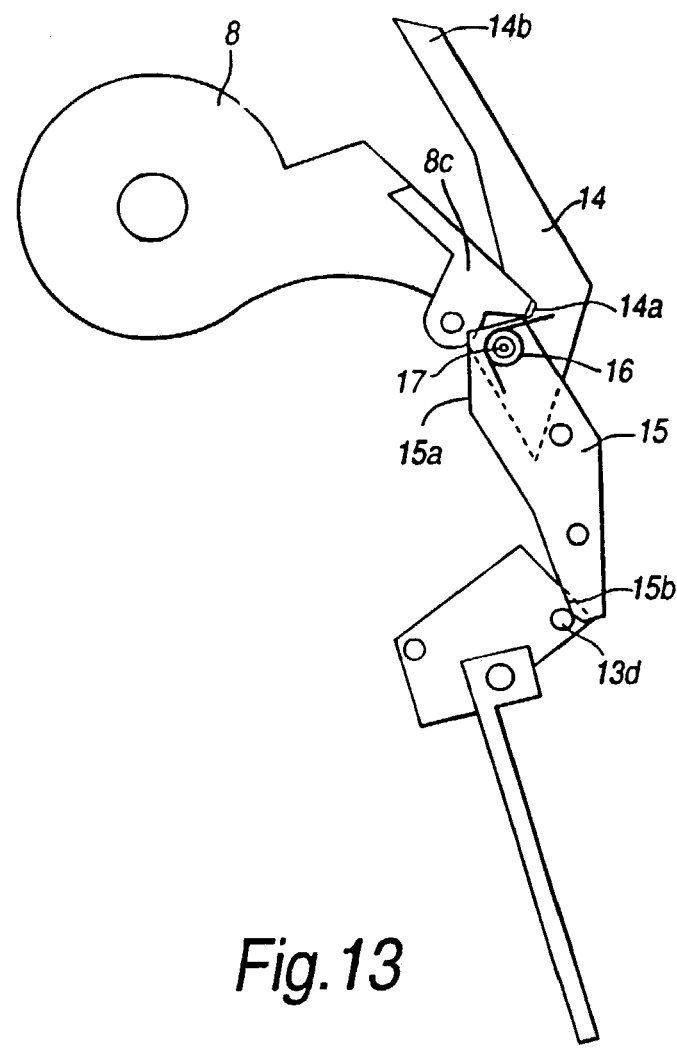
FIG. 13 is a side view of the locking mechanism.

As illustrated in FIG. 13, the actuation mechanism 6 further includes a locking mechanism for locking the spindle 8 after loading of the torsion spring 7. The locking mechanism comprises a catch 14 and an intermediate member 15 which are both pivotally mounted on the axle 17, adjacent the locking lever 12. Before compression of the canister 2, the intermediate member 15 is held in the position illustrated in FIG. 13 by the cross-piece 10*c* of the canister engagement lever 10 contacting a first contact surface 15*a* adjacent the axle 17. A resilient biasing element in the form of a torsion spring 16 is connected between the catch 14 and the intermediate member 15 and loaded to bias the catch 14 towards its locking position shown in FIG. 13.

The catch 14 has a notch 14*a* adjacent the axle 17 for engaging the arm 8*c* of the spindle 8 after rotation to the position illustrated in FIG. 13 where the torsion spring 7 is loaded. In this position, the loading provided by the spring 16 prevents release of the spindle 8 and thereby holds the torsion spring 7 in its loaded state. Before loading, the arm 8c of the spindle 8 is positioned above the end 14b of the catch 14 distal from the axle 17. When the spindle 8 is driven downwards by depression of the buttons 9, the arm 8c of the spindle engages the end 14b of the catch 14 and deflects the catch 14 by compressing the spring 16 to allow passage of the arm 8c of the spindle 8.

The flap 13 further includes a stud 13d protruding from the block 13b on the opposite side of the axle 18 from the locking lever engagement surface 13a. Upon inhalation at the mouthpiece 5, the flap 13 moves to the position illustrated in FIG. 13 where the stud 13d engages a second contact surface 15b of the intermediate member 15 distal from the axle 17. Prior to this point, the stud 13d does not contact the second contact surface 15b but the intermediate member 15 has been held in place by the canister engagement lever 10. Movement of the flap 13 triggers the triggering mechanism to release the canister engagement member 10 which moves downwards out of contact with the intermediate member 15. However, the stud 13d catches the contact surface 15b and so continues to hold the intermediate member 15 with the spring 16 loaded. Accordingly, the catch 14 remains in its locking position locking the spindle 8 by engagement of the arm 8c of the spindle 8 in the notch 14a of the catch 14.

Subsequently, when the level of inhalation of the mouthpiece falls below a predetermined threshold, the flap moves out of contact with the intermediate member 15 (clockwise in FIG. 13). The level of the predetermined threshold at which the flap 13 releases the intermediate member 15 is controlled by the shape of the second contact surface 15b of the intermediate member 15.

After release by the flap 13, the intermediate member 15 is driven by spring 16 which unloads (clockwise in FIG. 13). Such unloading of the spring 16 reduces the force by which the catch 14 is biased towards its locking position. Accordingly, the force of the torsion spring 7 acting on the canister engagement lever 10 is sufficient to force the catch arm 8c of the spindle 8 out of the notch 14a. Accordingly, the spindle 8, the torsion spring 7 and canister engagement lever 10 are able to move upwardly biased by the reset spring acting on the canister engagement lever 10, thereby allowing the canister to reset.

Figure 14A:
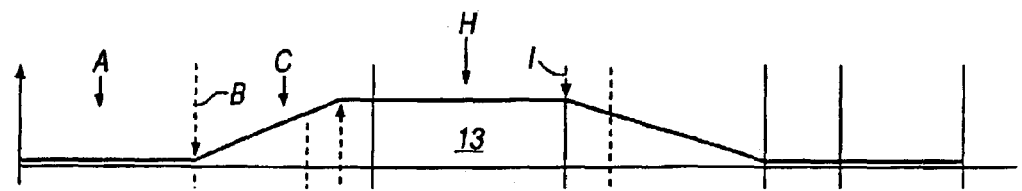
FIGS. 14A to 14F are graphs showing the angular positions of the elements of the actuation mechanism during its operation sequence.
Figure 14B:
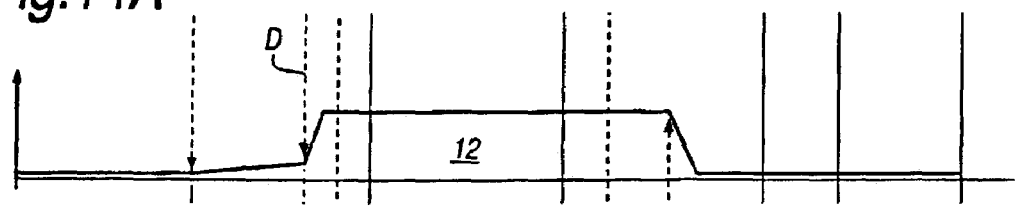
Figure 14C:
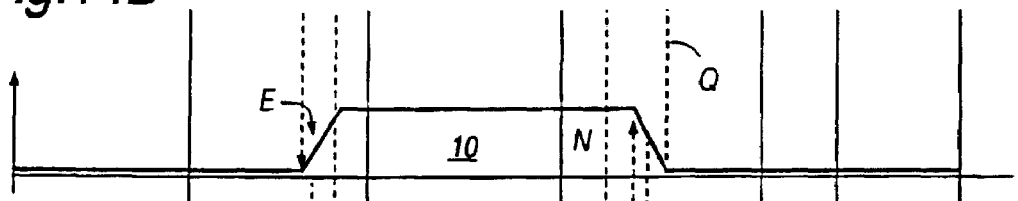
Figure 14D:
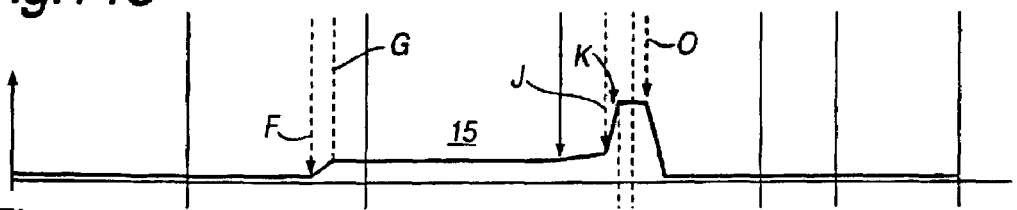
Figure 14E:
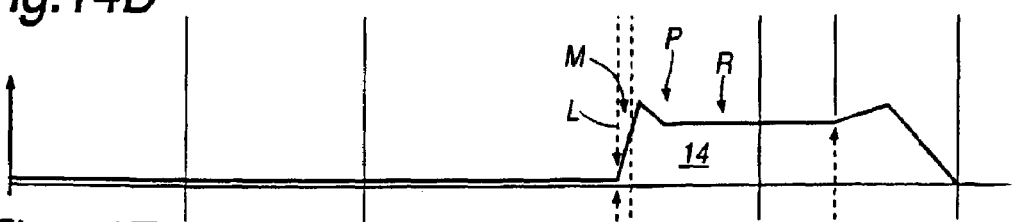
Figure 14F:
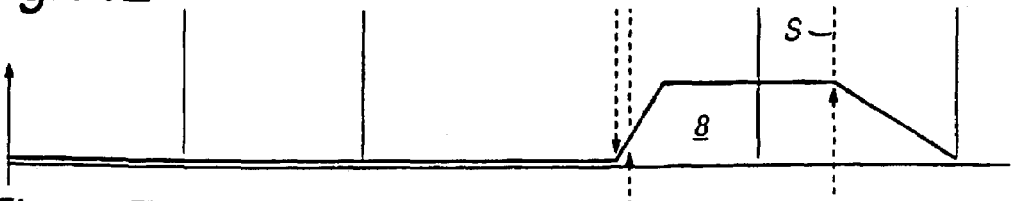

The sequence of operation of the actuation mechanism 6 will now be described with reference to FIGS. 14 to 22. FIGS. 14A to 14F are graphs showing the angular positions of the various elements of the actuation mechanism 6. In particular, FIG. 14A illustrates the angular position of the flap 13; FIG. 14B illustrates the angular position of the locking lever 12; FIG. 14C illustrates the angular position of the canister engagement lever 10; FIG. 14D illustrates the angular position of the intermediate member 15; FIG. 14E illustrates the angular position of the catch 14; and FIG. 14F illustrates the angular position of the spindle 8. Various states and positions of the actuation mechanism 6 are labelled by the letters A to R in FIGS. 14 and FIGS. 15 to 22 illustrate the actuation mechanism 6 in some of these states with the views from opposite sides being suffixed by the letters A and B, respectively.

Figure 15A:
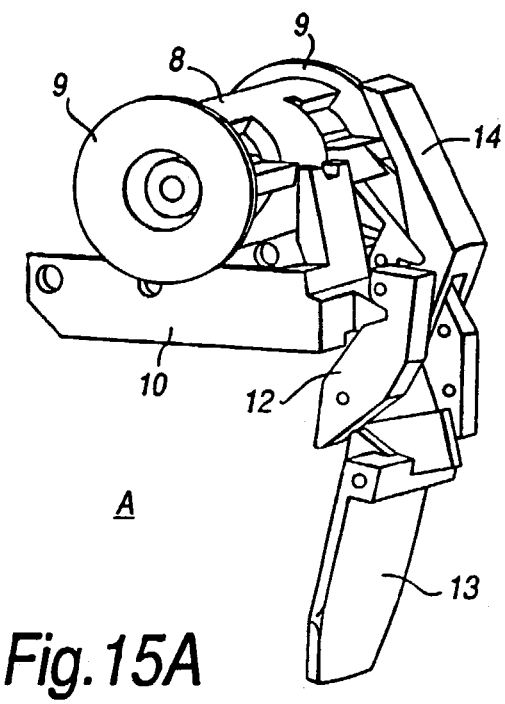
FIGS. 15 to 22 are views of the actuation mechanism in various states during its operation sequence with views from opposite sides being suffixed by the letters A, B respectively.
Figure 15B:
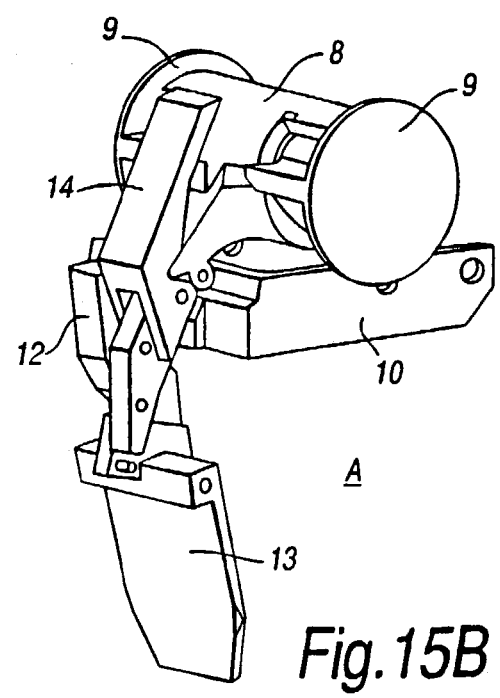
Figure 16A:
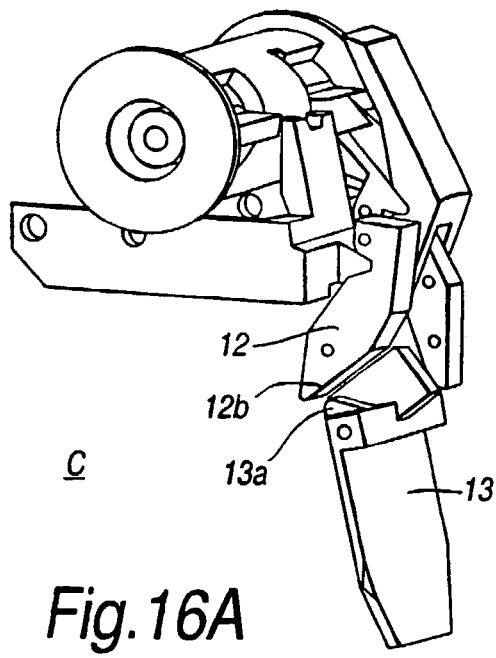
Figure 16B:
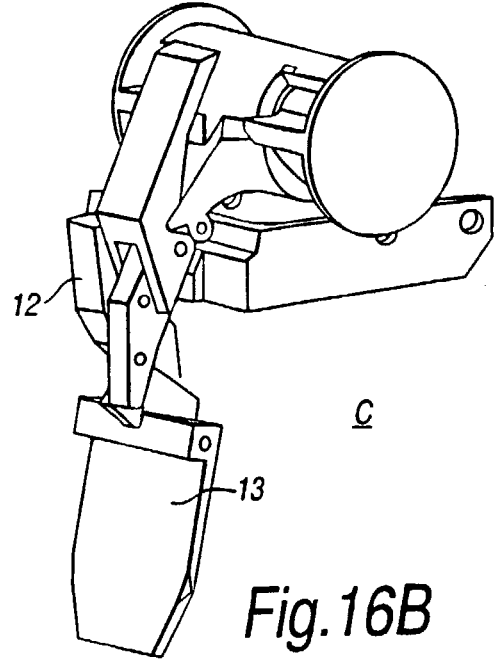
Figure 17A:
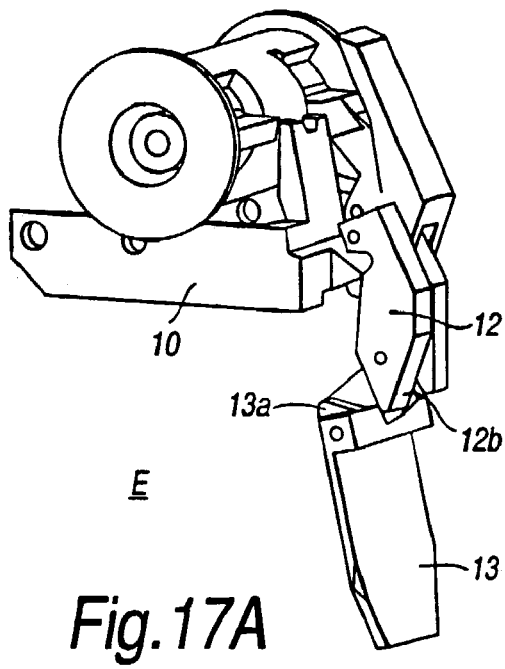
Figure 17B:
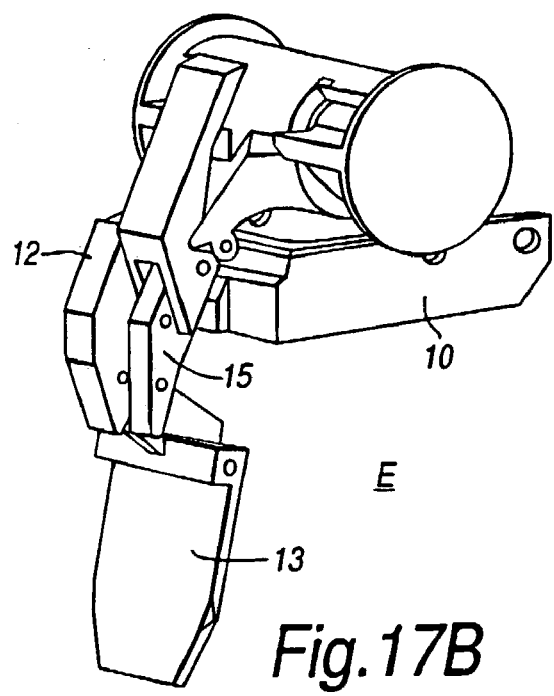
Figure 18A:
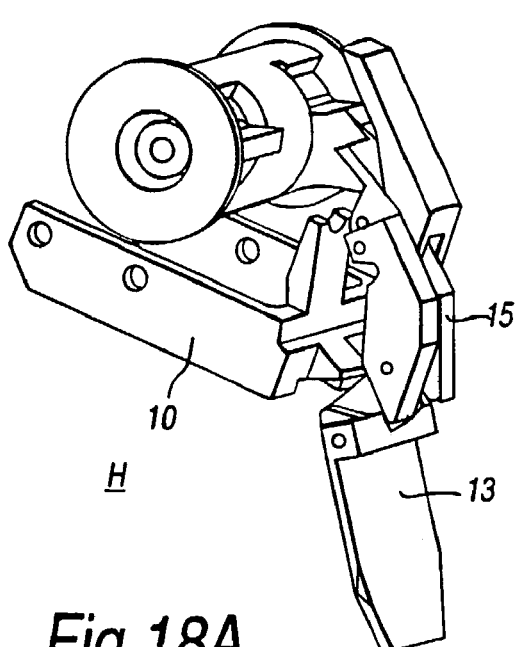
Figure 18B:
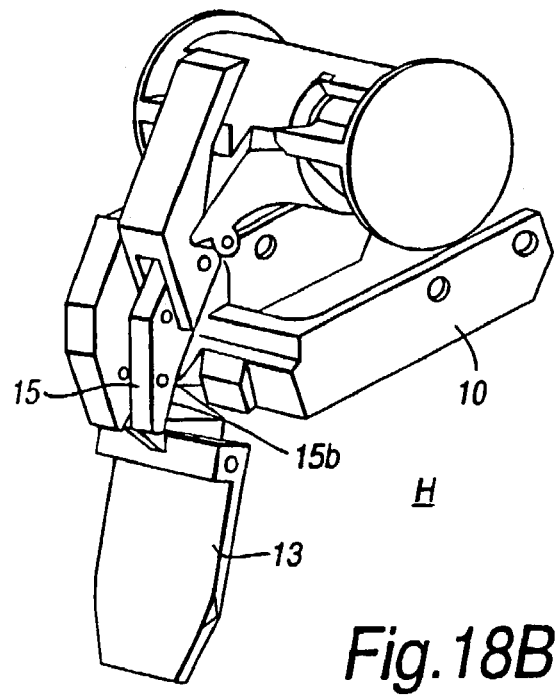
Figure 19A:
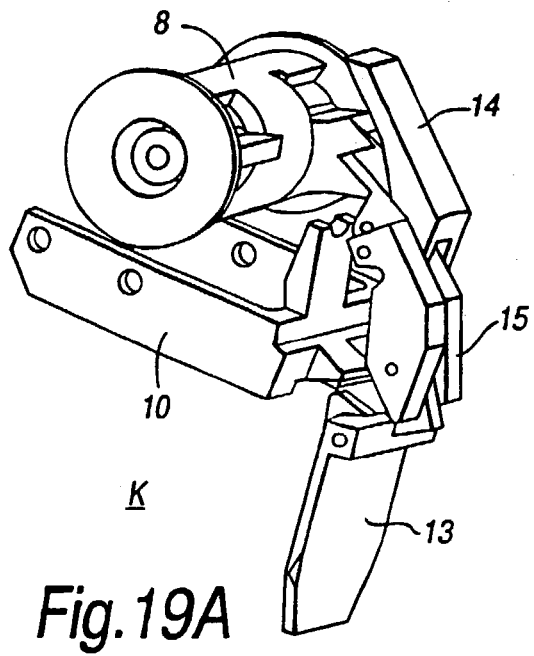
Figure 19B:
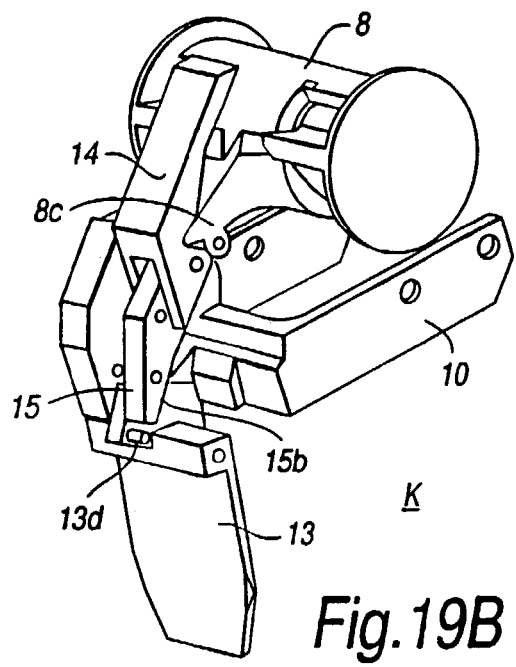
Figure 20A:
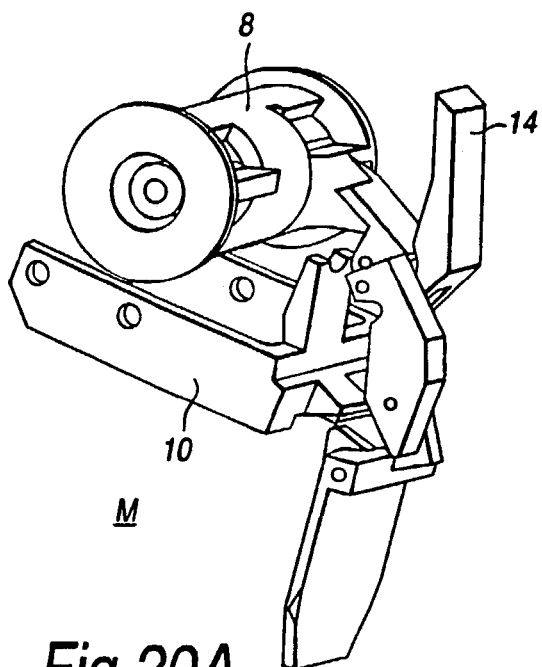
Figure 20B:
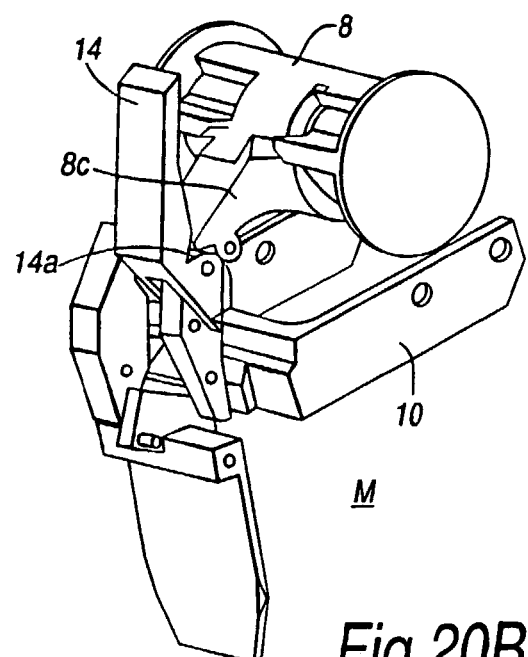
Figure 21A:
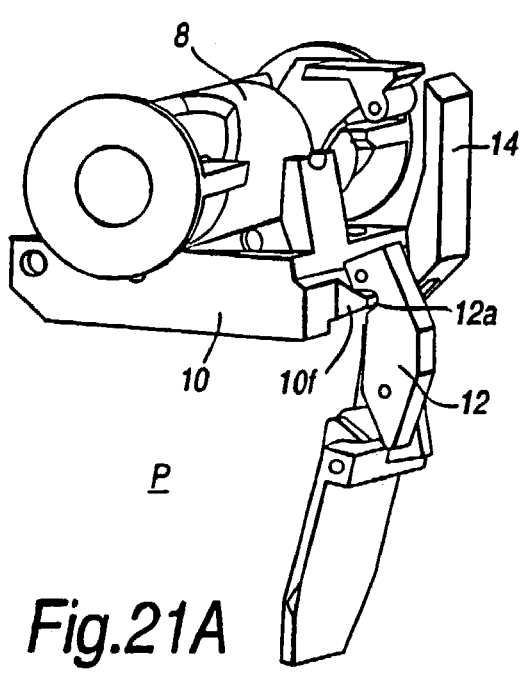
Figure 21B:
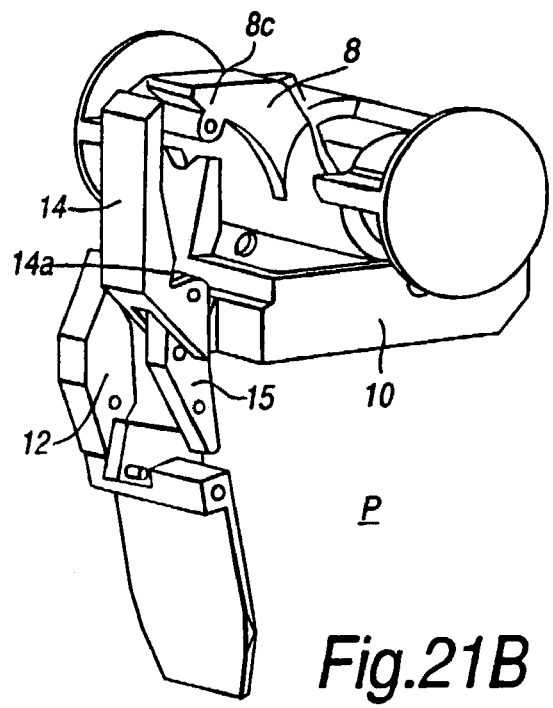
Figure 22A:
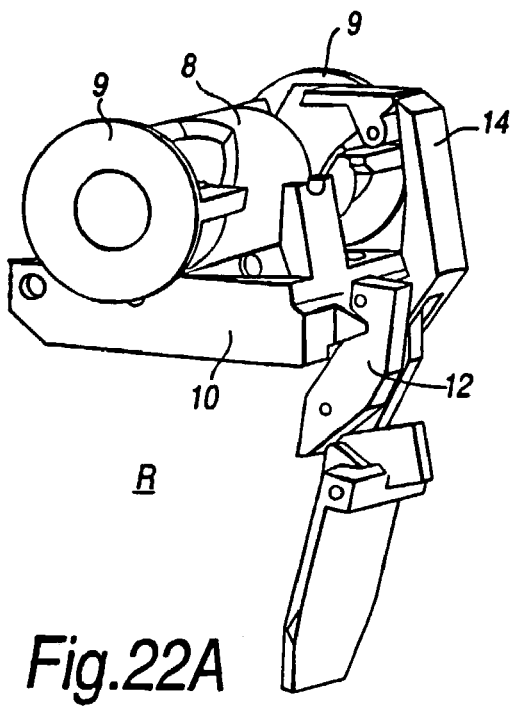
Figure 22B:
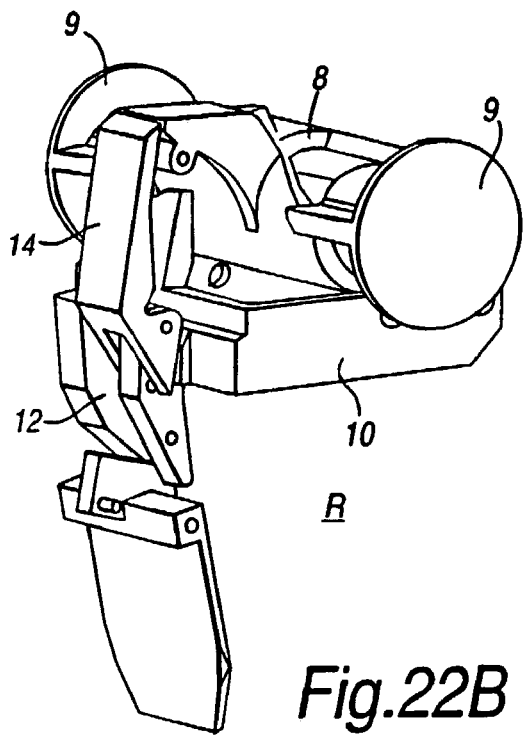

The sequence commences in state A as shown in FIG. 15 in which the torsion spring 7 has been loaded by depression of the buttons 9 and the spindle 8 is locked by the catch 14. In state A, the canister engagement lever is 10 held by the locking lever 12. The inhaler may be stored with the actuation mechanism 6 in state A.

At position B, the user starts to inhale. The flap 13, being responsive to such inhalation, starts to move. The shape of the contact surface 12b allows the locking lever 12 to start moving slowly. The actuation mechanism 6 is now in state C illustrated in FIG. 16.

At position D, the locking lever engagement surface 13a of the flap 13 releases the contact surface 12b of the locking lever 12. Accordingly, the canister engagement member 10 under the loading of the torsion spring 7 starts to rotate downwards deflecting the locking lever 12 against its reset spring as the projection 10f moves out of the notch 12a. The actuation mechanism is now in state E illustrated in FIG. 17.

At position F, the canister engagement lever 10 moves out of contact with the first contact surface 15a at the intermediate member 15 which therefore starts to move under the biasing of spring 16. However, the intermediate member 15 only moves a short way because at position G it is caught by the flap 13, in particular by the bar 13d of the flap 13 contacting the second contact surface 15b. This contact stops the movement of the flap 13 and the intermediate member 15.

The movement of the canister engagement lever 10 compresses the body 3 of the canister 2 relative to the stem 4 held in the nozzle block 11, thereby causing the canister 2 to deliver a dose of medicament. The nozzle block 11 directs the dose of medicament out of the mouthpiece at which the user is inhaling. The actuation mechanism 6 is now in state H illustrated in FIG. 18.

When the level of inhalation starts to fall, at position I the flap 13 under the biasing of its reset spring starts to move back closing the duct. This movement of the flap 13 causes the intermediate member 15 to move slightly due to the shape of the second contact surface 15b.

When the level of inhalation falls below the predetermined threshold, at position J the bar 13d of the flap 13 moves out of contact with the second contact surface 15b. This releases the intermediate member 15. Under the action of the spring 16, the intermediate member 15 moves to unload the spring 16. The actuation mechanism 6 is now in state K illustrated in FIG. 19.

At position L the load on the catch 14 from the spring 16 reduces to the extent that the catch 15 can no longer hold the spindle 8. The force of the torsion spring 7 forces the arm 8c of the spindle 8 upwards and out of engagement with the notch 14a of the catch 14. This forces the catch 14 backwards. The actuation mechanism 6 is now in state M illustrated in FIG. 20.

At position N, the torsion spring 7 reaches its neutral, unloaded position, so there is no load between the canister engagement lever 10 and the spindle 8. Thereafter the canister engagement lever 10 and the torsion spring 8 are moved under the action of the reset spring biasing the canister engagement lever 10.

At position O, the canister engagement lever 10 contacts the first contact surface 15a of the intermediate member 15 and forces it backwards. The actuation mechanism is now in state P illustrated in FIG. 21. This loads the spring 16 and pushes the catch 14 towards its locking position until the catch 14 contacts the arm 8c of the spindle 8 which has now passed out of the notch 14a.

At position Q, the projection 10f of the canister engagement lever 10 moves into the notch 12a of the locking lever 12 which snaps back into its locking position under the action of its reset spring. The actuation mechanism 6 is now in state R in FIG. 22. In state R, the canister is reset and ready to be compressed again for delivery of the next dose, but the actuation mechanism 6 is relaxed with the torsion spring 7 unloaded. The rotation of the spindle 8 has forced the buttons 9 outwards to the position illustrated in FIG. 22. The actuation mechanism 6 is ready to be loaded once again by compression of the buttons 9. The user is instructed to do this immediately after inhalation, so that the canister may be stored in a state ready to be used simply by inhaling at the mouthpiece 5.

When the user depresses the buttons 9 at position S, this drives the spindle 8 downwards. The arm 8c of the spindle 8 deflects the catch 14 slightly against the loaded spring 16 until the arm 8c moves into the notch 14a. This allows the spring 16 to snap the catch 14 into its locking position.

What is claimed is

1. An inhaler for delivery by inhalation of a medicament from a canister which is compressible to deliver a dose of medicament, the inhaler comprising
    a housing for holding a canister having a generally cylindrical body with the cylindrical axis of the body in predetermined direction;
    a loading mechanism for loading a resilient loading element which is arranged, when loaded, to bias compression of the canister, the loading mechanism comprising:
        a loading member engaging the resilient loading element; and
        at least one contact member movable relative to the housing in a movement direction orthogonal to said predetermined direction and arranged to drive the loading member to load the resilient loading element through a cam arrangement between the at least one contact member and the loading member.

2. An inhaler according to claim 1, having two contact members disposed on opposite sides of the housing.

3. An inhaler according to claim 2 wherein the two contact members comprise buttons configured to be pressed towards each other by a user of the inhaler.

4. An inhaler according to claim 1, wherein the cam arrangement includes at least one cam surface provided on the loading member and engaged by the at least one contact member.

5. An inhaler according to claim 1, wherein the loading member is driven to move in a direction orthogonal to said movement direction.

6. An inhaler according to claim 5, wherein the loading member is driven to rotate in said direction orthogonal to said movement direction.

7. An inhaler according to claim 5, wherein the resilient loading element is a torsion spring.

8. An inhaler according to claim 7, wherein the coils of the torsion spring encircle the loading member.

9. An inhaler according to claim 1, wherein the resilient loading element biases a canister engagement member engageable with a canister held in the housing to compress the canister.

10. An inhaler according to claim 1, wherein the canister engagement member is a lever rotatable about an axis parallel to the movement direction of the at least one contact member.

11. An inhaler according to claim 1, wherein the cam arrangement is arranged to hold the at least one contact member in place at the end of its movement.

12. An inhaler according to claim 1, wherein the ratio of the amount of driven movement of the loading member to the amount of movement of the at least one contact member being a non-linear function of the position of the loading member.

13. An inhaler according to claim 1, further comprising a triggering mechanism arranged to hold the resilient loading element against actuation of the canister and triggerable to release the resilient loading element.

14. An inhaler according to claim 13, wherein the triggering mechanism is arranged to be triggered by inhalation.

15. An inhaler according to claim 1 wherein the at least one contact member is exposed for contact by a user of the inhaler to load the inhaler.

16. An inhaler according to claim 15 wherein the at least one contact member is configured to be pressed in the movement direction by the user.

17. An inhaler according to claim 1 wherein the movement direction is parallel to a rotational axis of the contact member.

18. An inhaler for delivery by inhalation of a medicament from a canister which is compressible to deliver a dose of medicament, the inhaler comprising:
    a housing for holding a canister;
    a loading mechanism for loading a resilient loading element which is arranged, when loaded, to bias compression of the canister, the loading mechanism comprising:
        a loading member engaging the resilient loading element; and
        at least one contact member movable relative to the housing to drive the loading member to load the resilient loading element, the ratio of the amount of driven movement of the loading member to the amount of movement of the at least one contact member being a non-linear function of the position of the loading member.

19. An inhaler according to claim 18, wherein said ratio reduces during at least a major portion of the driven movement of the loading member.

20. An inhaler according to claim 19, wherein said ratio is inversely proportional to the position of the loading member during said major portion of its driven movement.

21. An inhaler according to claim 19, wherein said ratio varies with the position of the loading member during said major portion of the driven movement of the loading member such that the necessary force applied to the at least one contact member is substantially constant.

22. An inhaler according to claim 18, wherein said ratio is reduced during an initial portion of the driven movement of the loading member relative to the subsequent portion.

23. An inhaler according to claim 18, wherein the at least one contact member drives the loading member through a non-linear cam arrangement.

24. An inhaler according to claim 23, wherein the cam arrangement is arranged to hold the at least one contact member in place at the end of its movement.

25. An inhaler according to claim 23, wherein the cam arrangement includes at least one cam surface provided on the loading member and engaged by the at least one contact member.

26. An inhaler according to claim 25 wherein said cam surface has a non-linear shape configured so that the gearing ratio of the amount of driven movement of the loading member to the amount of movement of the at least one contact member is a non-linear function of the rotational position of the loading member.

27. An inhaler according to claim 25 wherein said cam surface is configured so that the necessary force applied to the contact member is substantially constant so that a user of the inhaler feels a linear resistance.

28. An inhaler according to claim 23, wherein the loading member is driven to move in a direction orthogonal to a movement direction of the at least one contact member.

29. An inhaler according to claim 28, wherein the loading member is driven to rotate in said direction orthogonal to said movement direction.

30. An inhaler according to claim 18, having two contact members disposed on opposite sides of the housing.

31. An inhaler according to claim 18, wherein the resilient loading element biases a canister engagement member engageable with a canister held in the housing to compress the canister.

32. An inhaler according to claim 18 wherein the at least one contact member is exposed for contact by a user of the inhaler to load the inhaler.

33. An inhaler according to claim 18 wherein the at least one contact member is configured for linear motion in said movement direction.

34. An inhaler according to claim 1 wherein the at least one contact member is configured for linear motion in said movement direction.

35. An inhaler according to claim 34 wherein the cam arrangement is configured to translate said linear motion of said contact member in said movement direction to rotational movement of the loading member in a direction orthogonal to said movement direction.

36. An inhaler according to claim 35 wherein the cam arrangement includes at least one non-linear cam surface and said contact member includes a cam follower configured to engage the cam surface and drive rotation of the contact member when the contact member moves in said movement direction.

37. An inhaler for delivery by inhalation of a medicament from a canister which is compressible to deliver a dose of medicament, the inhaler comprising
   a housing for holding a canister having a generally cylindrical body with the cylindrical axis of the body in predetermined direction;
   a loading mechanism for loading a resilient loading element which is arranged, when loaded, to bias compression of the canister, the loading mechanism comprising:
   a loading member engaging the resilient loading element; and
   at least one contact member, exposed for contact by a user of the inhaler to load the inhaler, the contact member being configured for linear movement relative to the housing in a movement direction orthogonal to said predetermined direction and arranged to drive the loading member to load the resilient loading element through a cam arrangement between the at least one contact member and the loading member.

38. An inhaler according to claim 37 wherein the cam arrangement is configured to drive rotation of said loading member in a direction orthogonal to said movement direction in response to movement of said contact member in said movement direction.

* * * * *

UNITED STATES PATENT AND TRADEMARK OFFICE
CERTIFICATE OF CORRECTION

PATENT NO. : 7,270,124 B2 Page 1 of 1
APPLICATION NO. : 10/221711
DATED : September 18, 2007
INVENTOR(S) : Jorgen Rasmussen It is certified that error appears in the above-identified patent and that said Letters Patent is hereby corrected as shown below:

Col. 11, line 48
In Claim 7, Line 1: Delete "5" and replace it with --6--.

Signed and Sealed this

Sixteenth Day of September, 2008

JON W. DUDAS
*Director of the United States Patent and Trademark Office*